(12) United States Patent
Behr

(10) Patent No.: US 9,901,656 B2
(45) Date of Patent: Feb. 27, 2018

(54) METHOD AND SYSTEM FOR CARPET-ODOR TREATMENT

(71) Applicant: Injectinator, LLC, Northfield, MN (US)

(72) Inventor: Jerome P. Behr, Northfield, MN (US)

(73) Assignee: Injectinator, LLC, Northfield, MN (US)

(*) Notice: Subject to any disclaimer, the term of this patent is extended or adjusted under 35 U.S.C. 154(b) by 0 days.

(21) Appl. No.: 15/376,415

(22) Filed: Dec. 12, 2016

(65) Prior Publication Data

US 2017/0157282 A1    Jun. 8, 2017

Related U.S. Application Data

(62) Division of application No. 14/340,419, filed on Jul. 24, 2014, now Pat. No. 9,517,285.

(60) Provisional application No. 61/873,350, filed on Sep. 3, 2013, provisional application No. 61/858,108, filed on Jul. 24, 2013.

(51) Int. Cl.
*A61L 9/14* (2006.01)
*B05B 11/00* (2006.01)
*B05B 11/04* (2006.01)

(52) U.S. Cl.
CPC ............ *A61L 9/14* (2013.01); *B05B 11/0089* (2013.01); *B05B 11/04* (2013.01)

(58) Field of Classification Search
CPC ........ A61L 9/14; B05B 11/04; B05B 11/0089
See application file for complete search history.

(56) References Cited

U.S. PATENT DOCUMENTS 4,109,340 A * 8/1978 Bates ...................... A47L 11/10
15/321

* cited by examiner

*Primary Examiner* — Regina M Yoo
(74) *Attorney, Agent, or Firm* — Charles A. Lemaire; Lemaire Patent Law Firm, P.L.L.C.

(57) ABSTRACT

The present invention provides a method and system for treating carpet that includes a hollow tube having a first end and a second end, wherein the tube further includes: a plurality of injection holes located near the second end of the tube, a pointed tip located at the second end of the tube, and a lug moveably attached to the tube; the method including inserting the tube into a carpet by penetrating the pointed tip into the carpet; lifting the tube up via the lug such that a portion of the carpet is pulled away from padding located underneath the carpet; and inserting fluid into the tube at the first end of the tube such that the fluid is injected into the carpet via the injection holes.

7 Claims, 17 Drawing Sheets

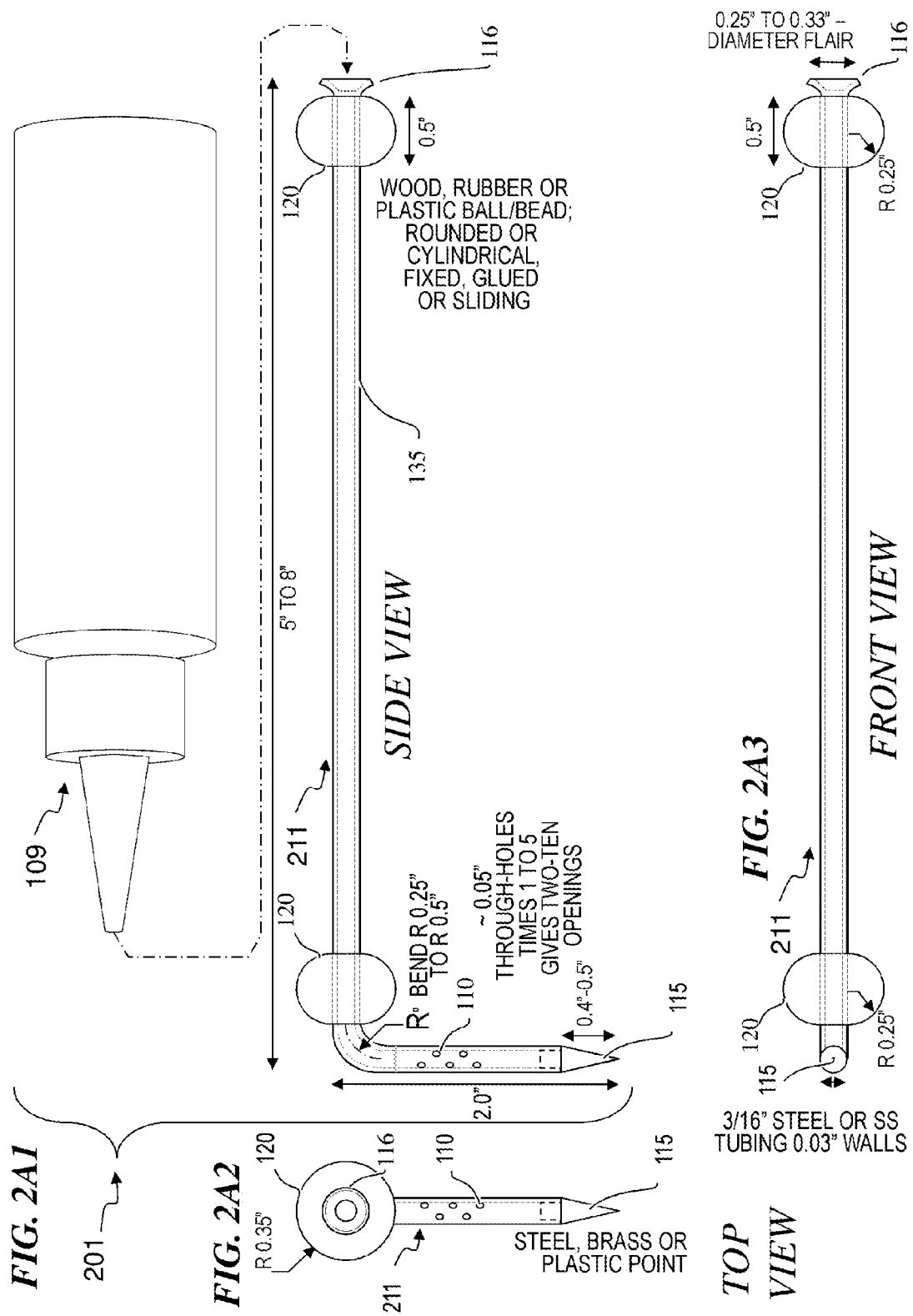

FIG. 2B2
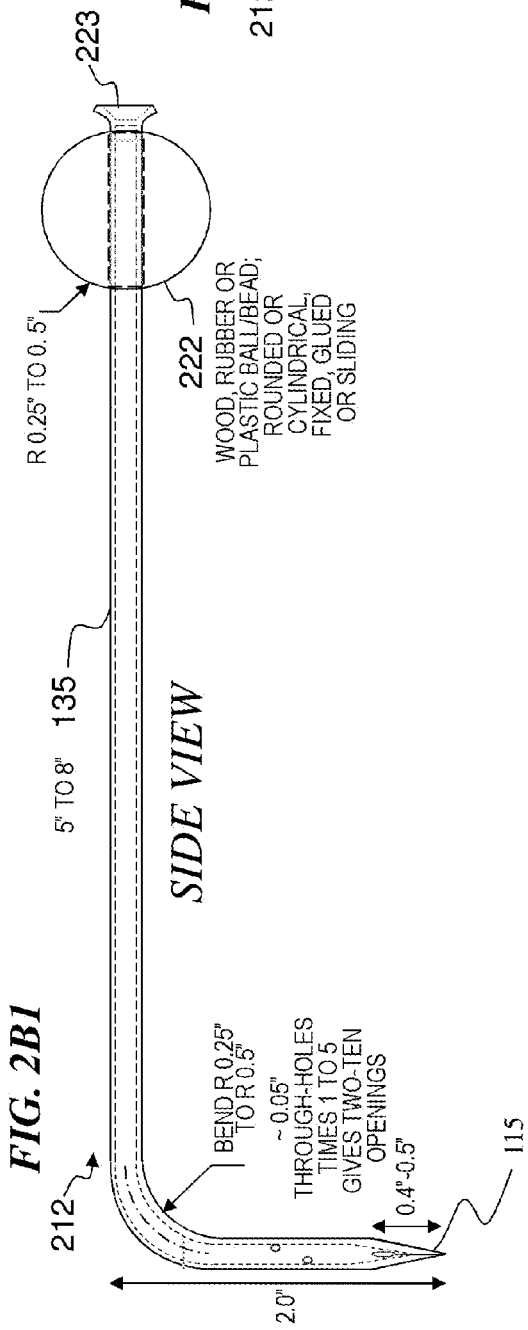
FIG. 2B1
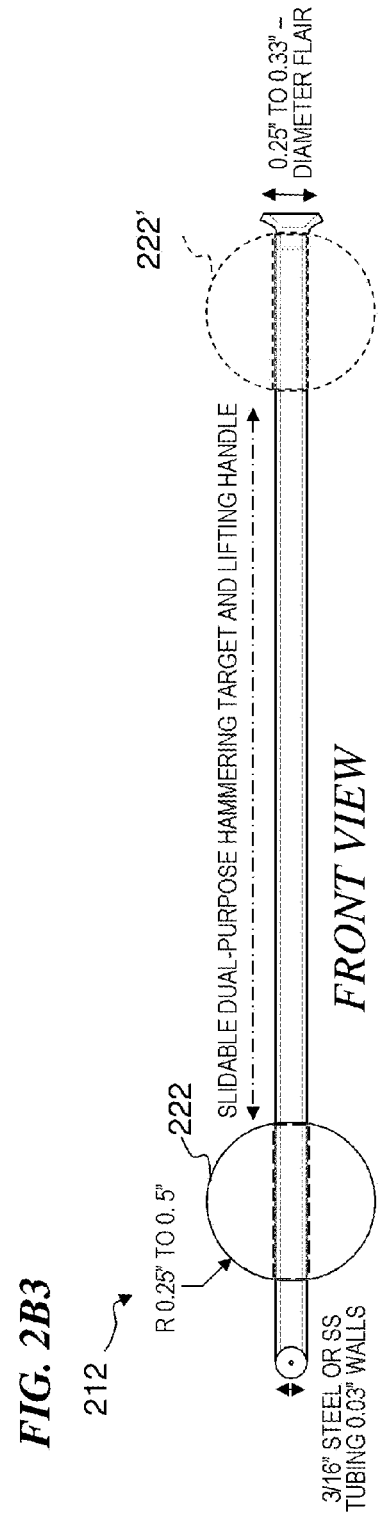
FIG. 2B3

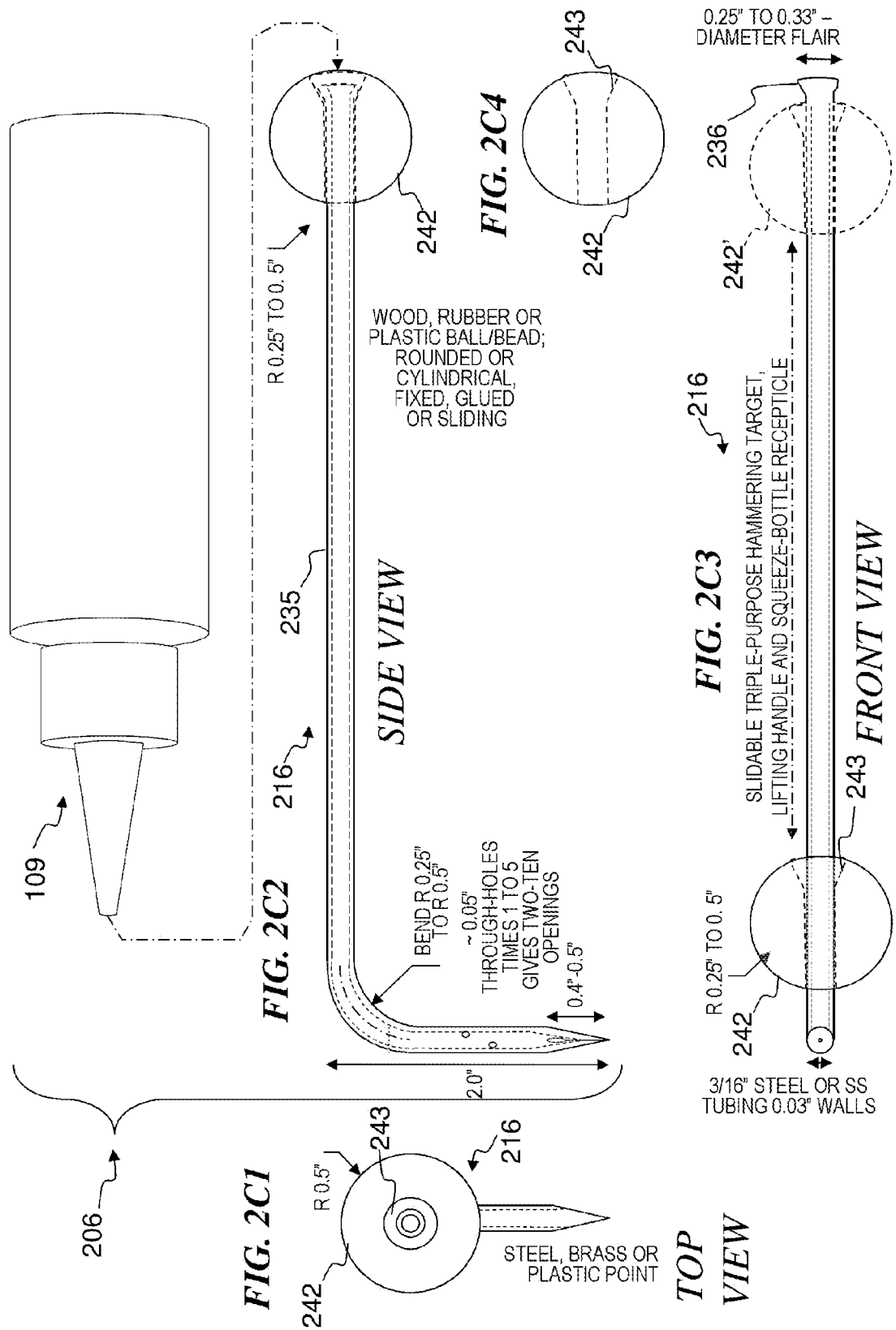

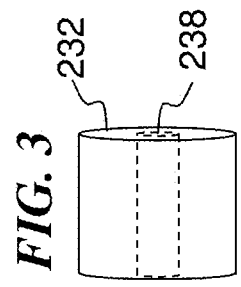
*FIG. 3*
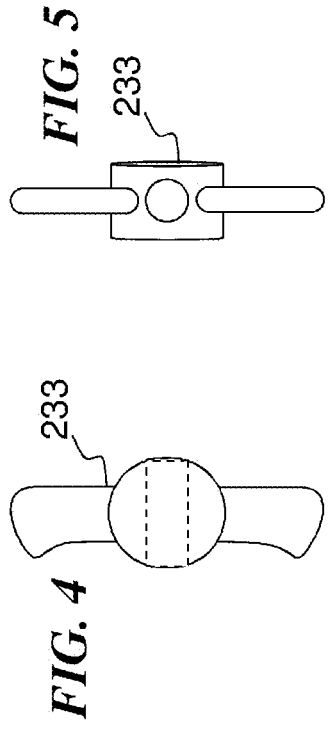
*FIG. 4*
*FIG. 5*
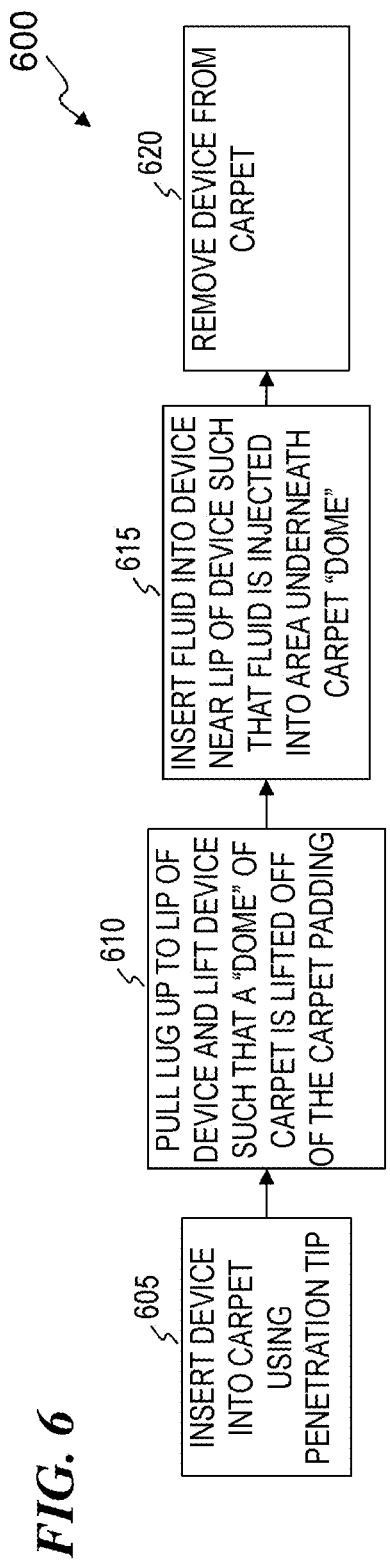
*FIG. 6*

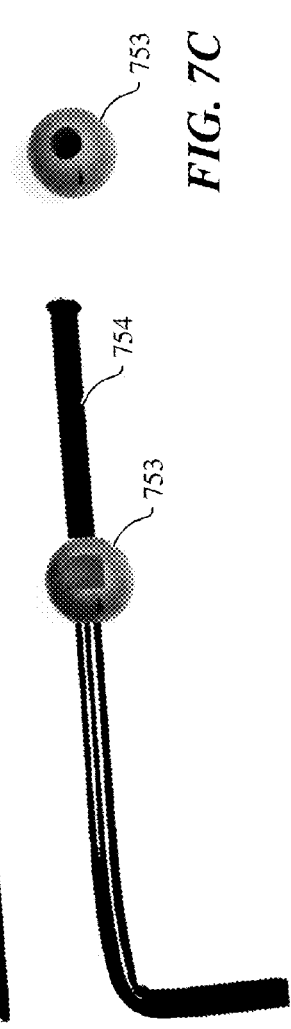
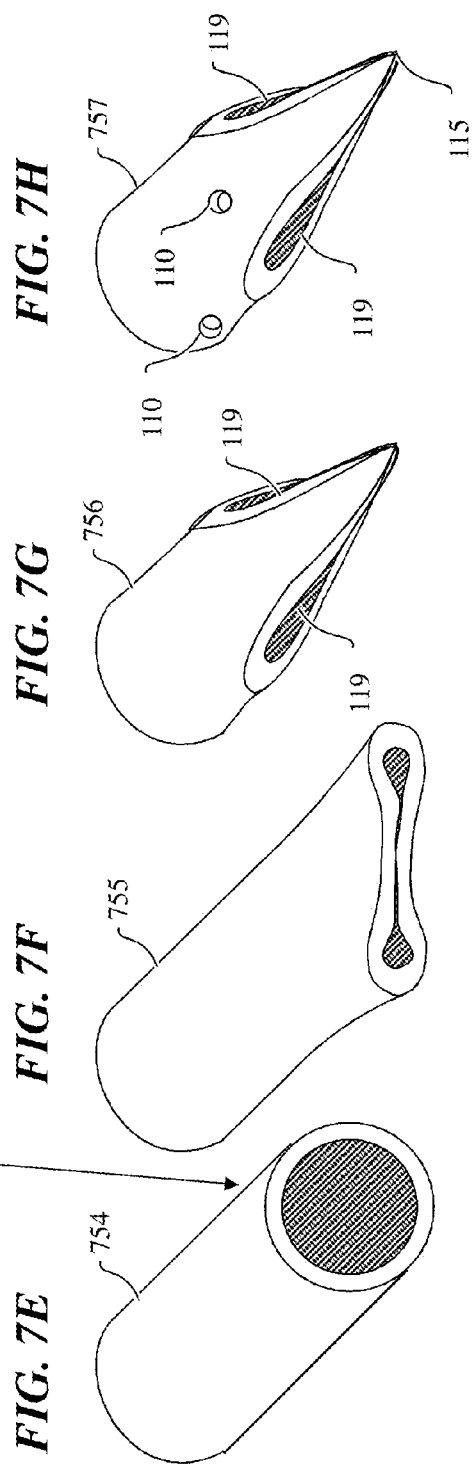
FIG. 7A
FIG. 7B
FIG. 7C
FIG. 7D
FIG. 7E
FIG. 7F
FIG. 7G
FIG. 7H

FIG. 7I1
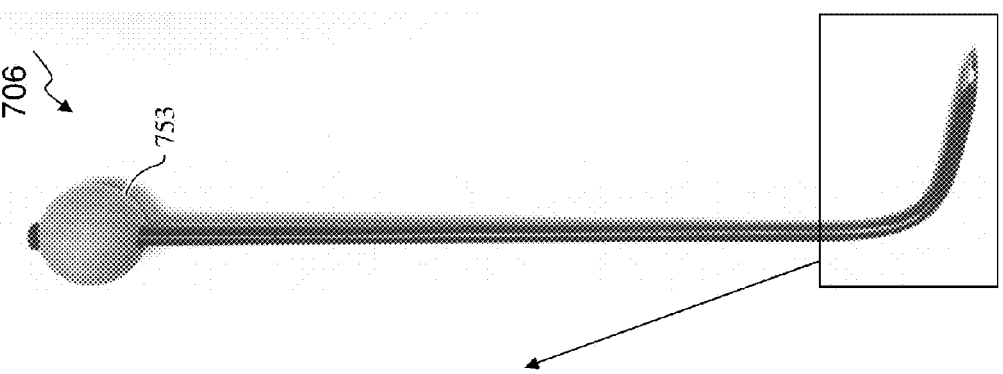
FIG. 7I2
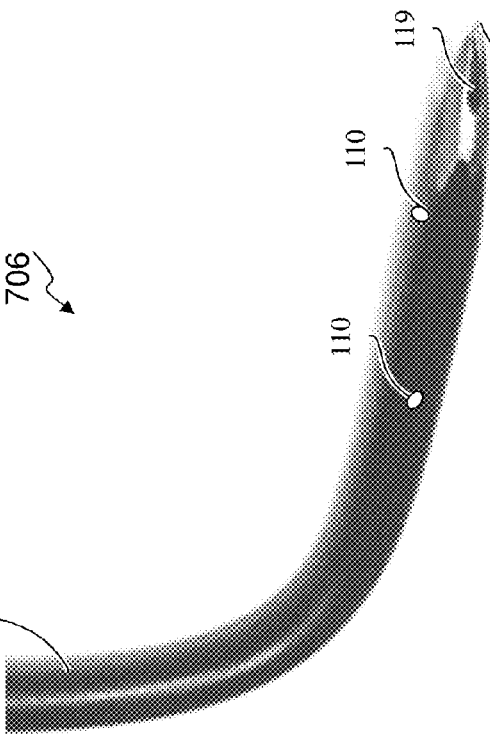
FIG. 7I3
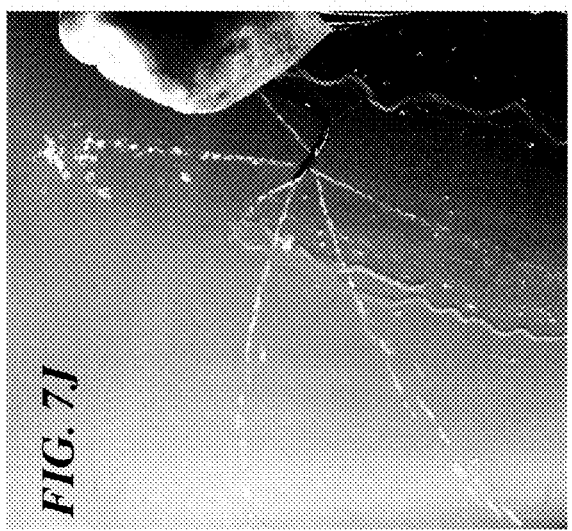
FIG. 7I

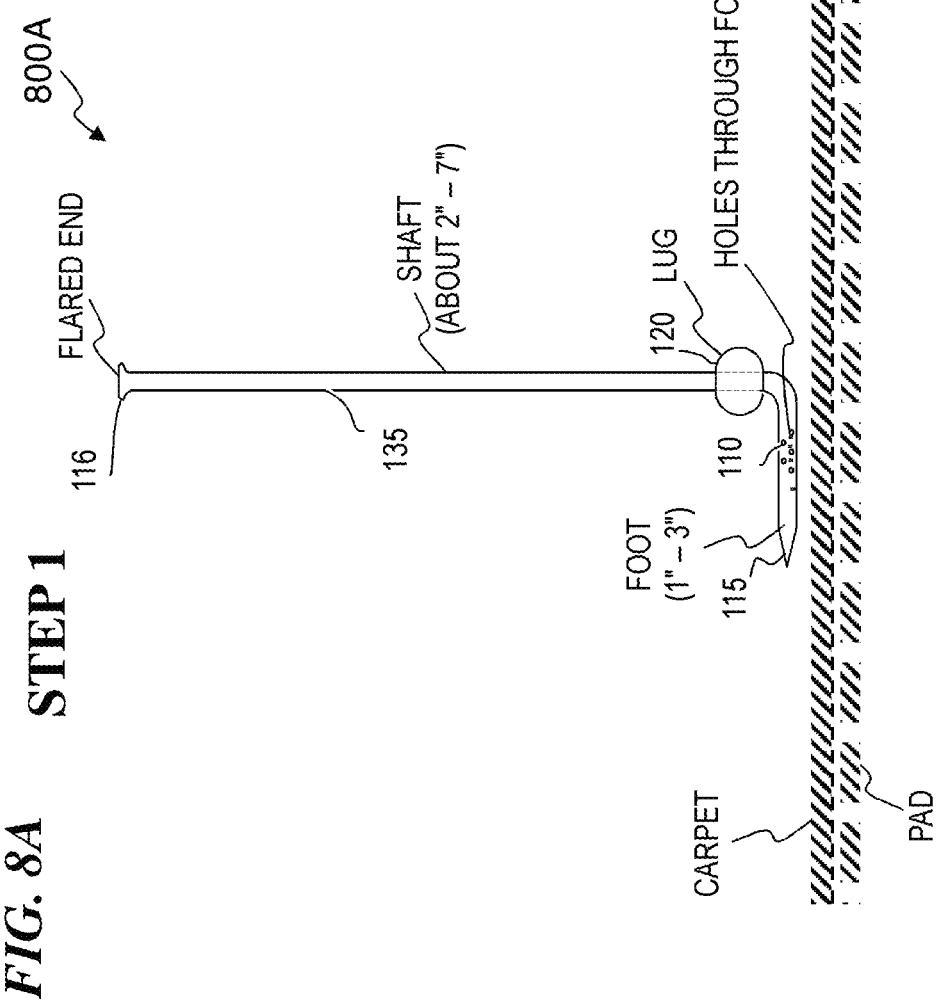
FIG. 8A   STEP 1

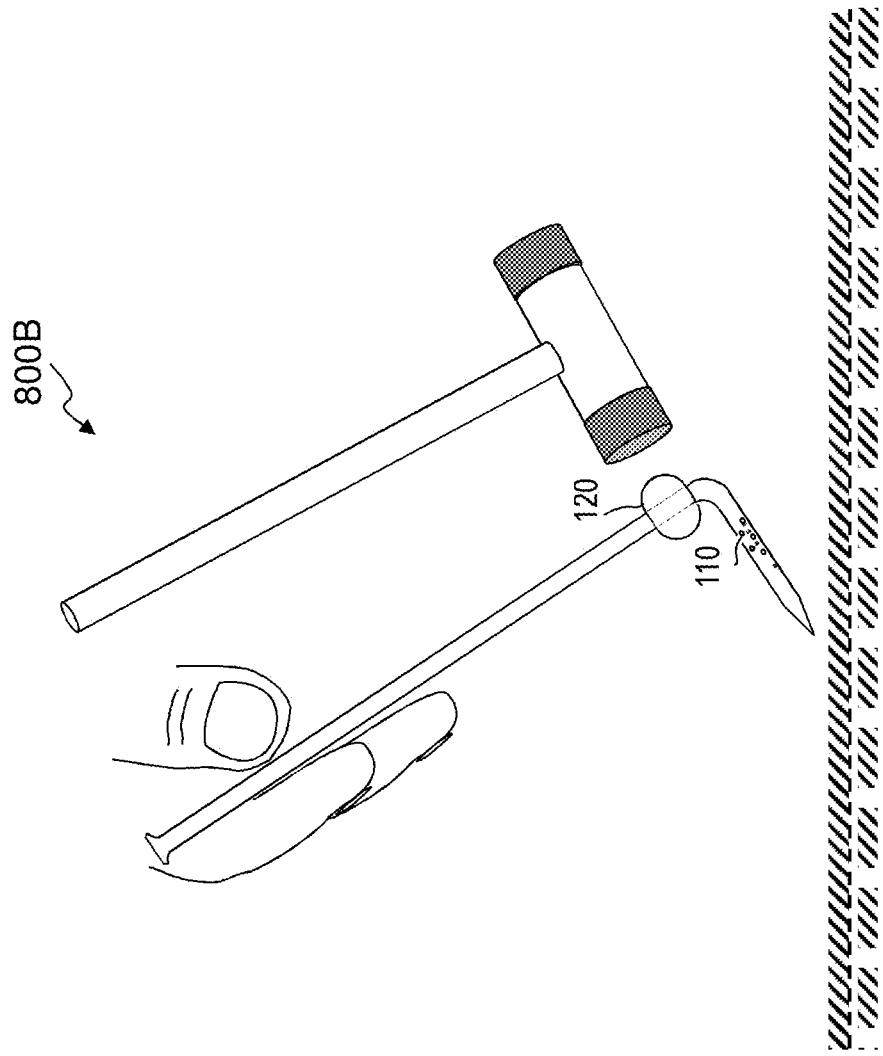

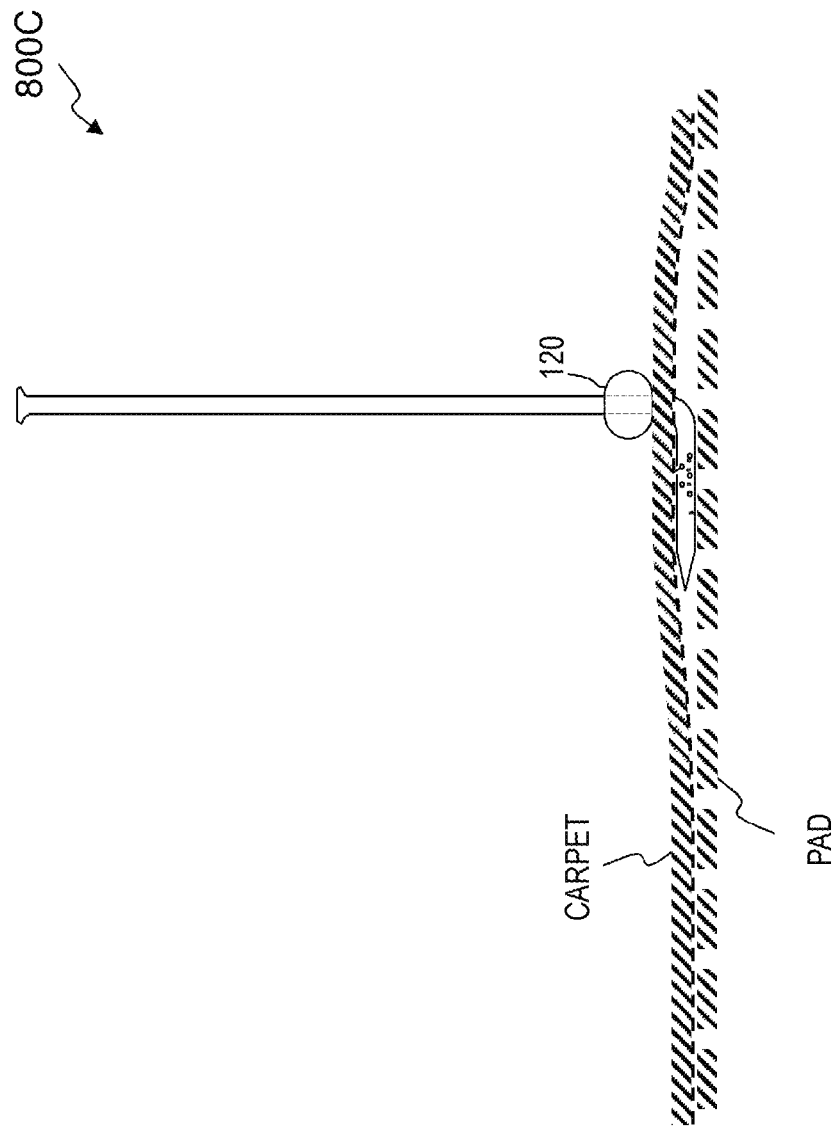

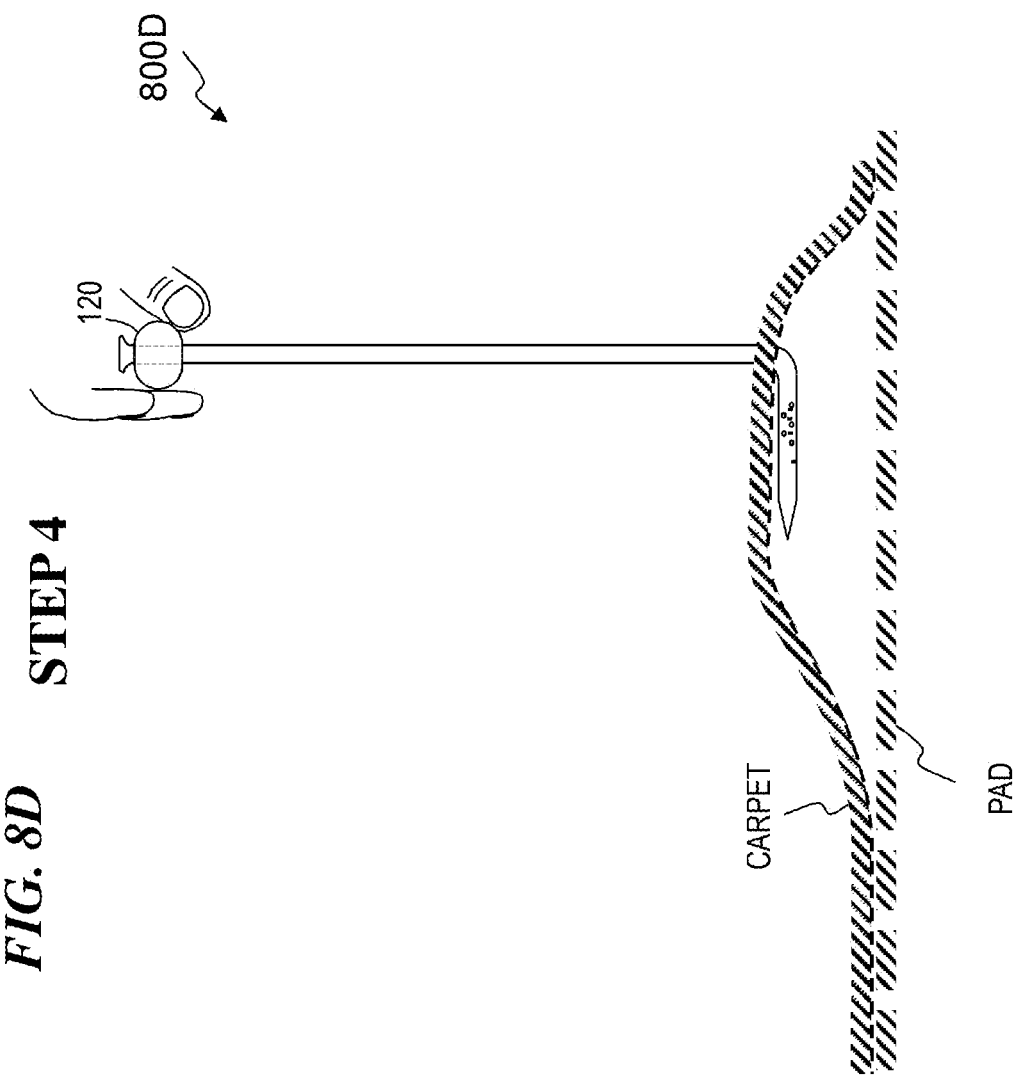
FIG. 8D  STEP 4

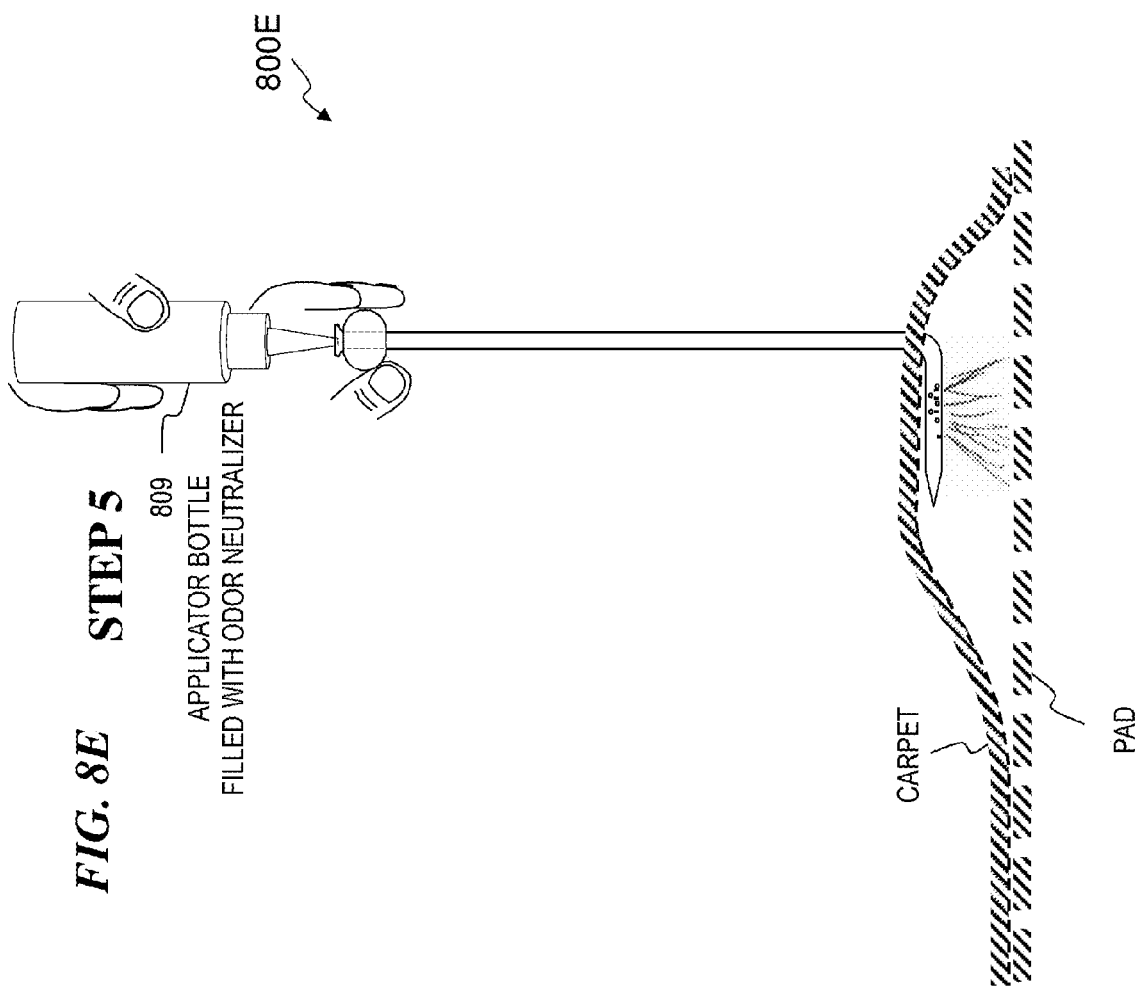

METHOD AND SYSTEM FOR CARPET-ODOR TREATMENT

CROSS-REFERENCE TO RELATED APPLICATIONS

This application is a divisional of U.S. patent application Ser. No. 14/340,419 filed Jul. 24, 2014 by Jerome P. Behr, titled "System and method for carpet-odor treatment" (which issued as U.S. Pat. No. 9,517,285 on Dec. 13, 2016), which claims priority benefit under 35 U.S.C. § 119(e) of U.S. Provisional Patent Application No. 61/858,108 filed Jul. 24, 2013 by Jerome P. Behr, titled "System and method for carpet-odor treatment," and of U.S. Provisional Patent Application No. 61/873,350 filed Sep. 3, 2013 by Jerome P. Behr, titled "Method and system for carpet-odor treatment," each of which is incorporated herein by reference in its entirety.

FIELD OF THE INVENTION

The present invention relates to fluid-delivery systems, and more particularly to devices and methods for treating carpet odors by delivering an anti-odor liquid underneath a carpet.

BACKGROUND OF THE INVENTION

Carpet odors (e.g., an odor associated with a pet that has urinated on the carpet) are often caused by an odorous liquid that has soaked through the carpet and down into the padding located directly below the carpet. Accordingly, a standard method for treating carpet odors is to inject an odor-neutralizing fluid into the carpet at the source of the odorous liquid using a hypodermic needle. This method limits the coverage area of the injected fluid to the small area immediately surrounding the needle tip. Hypodermic-needle methods also make it difficult to direct the odor-neutralizing fluid to the carpet padding because it can be hard to judge the carpet thickness and the penetration depth of the hypodermic needle when inserting the hypodermic needle into the carpet.

U.S. Pat. No. 4,109,340 to Leonard Eugene Bates (hereinafter, "Bates"), titled "Truck mounted carpet cleaning machine," issued Aug. 29, 1978, and is incorporated herein by reference. Bates describes a carpet cleaning machine mounted on a truck or van for transport to the work site. The main power for the machine is developed by an internal combustion engine which drives an injection pump, a vacuum pump, and a sump pump. A reservoir maintains and stores a supply of cooling water-cleaning fluid for removing heat generated by the engine. Coolant-cleaning fluid is drawn from the engine by the injection pump for transmission to the carpet cleaning injection nozzles. The coolant may be further heated as it is drawn from the engine by means of a heat exchanger which removes heat from the engine exhaust gases. The coolant may be further heated by deliberately employing an inefficient injection pump. The vacuum pump draws water from the carpet through a filter or sump which may be discharged through the sump pump when a predetermined coolant level is achieved in the sump. Make-up water may be delivered to the reservoir by a float-actuated valve which directs the make-up water through a venturi operative to inject a cleaning agent or solvent into the water. When the machine is not actually in carpet cleaning use, a temperature actuated valve may deliver coolant from the reservoir directly to the sump pump for discharge, thus preventing overheating of the engine.

U.S. Pat. No. 4,336,627 to Lionel D. Bascus (hereinafter, "Bascus"), titled "Water conditioning systems," issued Jun. 29, 1982, and is incorporated herein by reference. Bascus describes a system for conditioning and dispersing wash water which is particularly suited for mobile carpet cleaning. The system comprises a liquid cooled internal combustion engine operating a high pressure pump, a water supply tank feeding water to the high pressure pump, a pulse pump for injecting chemicals into the water, an immersion heat exchanger downstream of the high pressure pump and a tool, which can be in the form of a cleaning wand when used for carpet cleaning, from which the chemically treated and heated water is dispersed onto a surface to be cleaned.

U.S. Pat. No. 4,949,424 to William Shero (hereinafter, "Shero"), titled "Carpet cleaning system," issued Aug. 21, 1990, and is incorporated herein by reference. Shero describes an apparatus that consists of an internal combustion engine, the exhaust of which is directed through at least one heat exchanger for heating water/chemical cleaning fluid solution. A source of incoming water passes by a regulator into the inlet end of an engine driven pump, then through a balance pressure regulator valve positioned between the pump and the heat exchanger. A bypass valve intercepts a portion of the heated water after it passes by a thermostat downstream of the heat exchanger and directs this portion of heated water into a conduit leading back to the pump inlet thereby preheating the incoming water. A vacuum pump coupled to the engine draws a vacuum in a separate waste water recovery tank. A hand held carpet cleaner wand injects heated water transported under pressure through a flexible hose through an exhaust nozzle into the surface being cleaned. A vacuum intake port adjacent the exhaust nozzle of the wand vacuums up the residual fluid and directs the fluid back to the recovery tank through another flexible hose. The constantly circulating heated bypass water reduces stagnation of water in the heat exchanger when the wand is deactivated thereby effectively preventing a complete shut down of the system due to overheated water sensed by the thermostat in the heat exchanger.

U.S. Pat. No. 5,048,148 to Robert Gleadall (hereinafter, "Gleadall"), titled "Carpet cleaning apparatus," issued Sep. 17, 1991, and is incorporated herein by reference. Gleadall describes a carpet cleaning apparatus consisting of a housing having a lower surface and an interior cavity. Wheels are secured adjacent to the lower surface of the housing. A conduit is secured to the housing. The conduit has a first end whereby the conduit may be coupled to a water supply and a second end with spray jets whereby fluids may be injected into a carpet. A discharge tank is secured within the interior cavity of the housing. The discharge tank has two suction ports, and two fluid inlets. Two suction conduits are provided. Each suction conduit has a first end communicating with one of the fluid inlets of the discharge tank and a second end disposed adjacent the lower surface of the housing. Two suction motors are secured in the interior cavity of the housing, each of the suction motors communicating with one of the suction inlets of the discharge tank such that a vacuum is created within the discharge tank and the suction conduits. Discharge fluids are drawn from the surface of a carpet via the suction conduits into the fluid inlets of the discharge tank.

U.S. Pat. No. 6,014,790 to David A. Smith et al. (hereinafter, "Smith et al."), titled "Ductwork cleaning system," issued Jan. 18, 2000, and is incorporated herein by reference. Smith et al. describe a system for cleaning building ductwork utilizing the equipment generally used to clean carpets. The system utilizes the vacuum unit and liquid waste tank from a carpet cleaning system. A flexible hose runs between the waste tank and the building ductwork. A water injection system is connected to the hose and is used to spray a stream of water into the air flowing through the flexible ductwork which will entrap any particles contained therein. The "dirty" water flowing out of the hose will flow to the waste tank for collection and disposal.

U.S. Patent Application Publication 2008/0256745 to Nicola Santoemma et al. (hereinafter, "Santoemma et al."), titled "Moquette carpet cleaning machine operable in pull-back mode," published Oct. 23, 2008, and is incorporated herein by reference. Santoemma et al. describe a moquette carpet cleaning machine (10) operable in pull-back mode comprising a machine body (11) provided with main rear wheels (12) and a suction mouth (14) placed at the front and is characterised in that support means (19) are constrained to the machine (10), on which support means (19) at least one auxiliary wheel (16) is mounted, and in that at least one from among the main wheels (12), suction mouth (14), the at least one auxiliary wheel (16) and support means (19) are movable means with respect to the machine body (11), between at least a first (A) and at least a second (B) relative position such that, when the movable means (12,14,19,16) are in the first relative position (A), the suction mouth (14) is maintained adherent to the ground (20), and when the movable means (12,14,19,16) are in the second relative position (B), the suction mouth (14) is maintained substantially raised from the ground (20).

U.S. Patent Application Publication 2010/0000043 to Don M. McNulty (hereinafter, "McNulty"), titled "Carpet cleaning fluid injection apparatus," published Jan. 7, 2010, and is incorporated herein by reference. McNulty describes a carpet cleaning fluid injection apparatus for adaptation to a vacuum nozzle. The injection apparatus configured to surround the vacuum nozzle for purposes of injecting the cleaning fluid into the carpet in proximity to the vacuum nozzle and the vacuum nozzle configured for extracting the cleaning fluid from the carpet.

PCT Application PCT/DK94/00390 (published as WO 95/10972 A1) to Jörgren Sjögreen (hereinafter, "Sjögreen"), titled "Universal vacuum cleaner," published Apr. 27, 1995, and is incorporated herein by reference. Sjögreen describes a universal vacuum cleaner, which without disassembly or exchange of parts, free of choice can be used for dry vacuum cleaning, wet vacuum cleaning, carpet cleaning, floor wash and to suck up water from kitchen sinks and the like. The universal vacuum cleaner works by injecting water, to which may be added a detergent, in the sucked in air stream through a system of nozzles (21 and 22), after which foreign matters are wetted by water and detergents. The coarse foreign matters are picked up in a detachable pick up tray (7) including a coarse filter (8), from which the liquid is drained to the below placed detachable liquid container (4). The smaller foreign matters and the water are separated from the air in a cyclone (15), accumulated in a liquid pump (16), which pumps the water and foreign matters return to the liquid container (4), whereas the dry and dust free air escapes through the opening (24) in the top of the cyclone (15). The detergent recirculates constant by the liquid pump (17). The liquid container (4), containing the dirty water, is taken out and emptied in a sink, when the vacuum cleaning is finished, washed out and refilled with clean water at next vacuum cleaning.

European Patent Application Publication EP 1 106 566 A1 to the Proctor & Gamble Company (hereinafter, "Proctor & Gamble"), titled "Container connector with piercing means," published Jun. 13, 2001, and is incorporated herein by reference. Proctor & Gamble describe a reservoir for use with a dispensing appliance for spraying a liquid is provided, wherein the dispensing appliance comprises a protecting plate and at least two needles for engaging the reservoir. The protecting plate has a locked position and an unlocked position, wherein the protecting plate is movable in the unlocked position to expose the needles and is immovable in the locked position. The reservoir comprises a finish with an opening which communicates with the interior of the reservoir and a membrane disposed across the opening, wherein the membrane has an exposed length of less than about 45 mm.

There is a need for an improved system and method for treating carpet odors.

SUMMARY OF THE INVENTION

In some embodiments, the present invention provides a carpet-treatment device having a fluid-receiving first end and a carpet-piercing pointed second end. The device also includes an impact- or force-reception feature configured to receive force (e.g., hammer blows or pressure from the heel of the hand of the human user) and to deliver that force toward the pointed second end in order to pierce carpet and carpet backing. The device also includes a plurality of injection perforations (e.g., holes or other fluid-permeable passageways) located near the second end of the tube. The pointed tip (the carpet-piercing pointed end) is at the second end of the tube, and a fluid-receiving feature (e.g., a cone or funnel-shaped end configured to receive the tip of a fluid squeeze bottle and configured to convey the fluid is located at the first end of the tube. A lifting feature attached to the tube provides a grip by which the user can lift the carpet and its backing so that the fluid is sprayed from the injection perforations onto the underside of the carpet and carpet backing that is being held above the pointed second end, and the fluid also sprays onto the carpet pad underneath the pointed second end.

In some embodiments, the present invention provides a carpet-treatment device that includes a hollow tube having a first end and a second end; a plurality of injection holes located near the second end of the tube; a pointed tip located at the second end of the tube; and a lug moveably attached to the tube and configured to increase the graspable diameter of the tube (to make it easier to grab and pull up on the tube).

In some embodiments, the present invention provides a method for treating carpet that includes providing a hollow tube having a first end and a second end, wherein the tube further includes: a plurality of injection holes located near the second end of the tube, a pointed tip located at the second end of the tube, and a lug moveably attached to the tube; the method further including inserting the tube into a carpet by penetrating the pointed tip into the carpet; lifting the tube up via the lug such that a portion of the carpet is pulled away from padding located underneath the carpet; and inserting fluid into the tube at the first end of the tube such that the fluid is injected into the carpet via the injection holes at the second end of the tube.

BRIEF DESCRIPTION OF THE FIGURES

FIG. 2A1 is a side-view diagram of a carpet-odor-treatment system 201 that includes carpet-odor treatment device 211 and deodorizer-fluid-dispensing squeeze bottle 109.

FIG. 2A2 is a top-view diagram of carpet-odor-treatment device 211.

FIG. 2A3 is a front-view diagram of carpet-odor-treatment device 211.

FIG. 2B1 is a side-view diagram of a carpet-odor-treatment device 212.

FIG. 2B2 is a top-view diagram of carpet-odor-treatment device 212.

FIG. 2B3 is a front-view diagram of carpet-odor-treatment device 212.

FIG. 2C1 is a side-view diagram of a carpet-odor-treatment system 206 that includes carpet-odor treatment device 216 and deodorizer-fluid-dispensing squeeze bottle 109.

FIG. 2C2 is a top-view diagram of carpet-odor-treatment device 216.

FIG. 2C3 is a front-view diagram of carpet-odor-treatment device 216.

FIG. 2C4 is a side-view diagram of a carpet-odor-treatment device combination funnel-shaped-fluid-receiving, force-delivery and lifting element 233.

FIG. 3 is a perspective side-view diagram of a cylindrical carpet-odor-treatment device combination force-delivery and lifting element 232.

FIG. 4 is a side-view diagram of a cylindrical carpet-odor-treatment device combination force-delivery and lifting element 233.

FIG. 5 is a top-view diagram of a cylindrical carpet-odor-treatment device combination force-delivery and lifting element 233.

FIG. 6 is a block diagram of a method for using device 100 to treat a carpet with an odor-neutralizing fluid.

FIG. 7A is a side-view photograph of an open-ended steel tube 751 before further processing according to some embodiments of the present invention.

FIG. 7B is a side-view photograph of an open-ended steel tube 752 after a flare has been formed at the right-hand end.

FIG. 7C is an end-view photograph of a wooden ball 753 having a through-hole.

FIG. 7D is an end-view photograph of open-ended steel tube 754 after a flare has been formed at the right-hand end, a wooden ball 753 having a through-hole fitted over the tube 754, and a rounded bend of about 90 degrees formed near the left-hand end.

FIG. 7E is an end-perspective-view drawing of the left-hand end of steel tube 754.

FIG. 7F is an end-perspective-view drawing of the left-hand end of steel tube 755 after being partially flattened with a taper.

FIG. 7G is an end-perspective-view drawing of the left-hand end of steel tube 756 after being partially flattened with a taper, and then ground or sanded to a point, which results in two angled openings 119 that emit fluid at about a 30-degree angle to one another forward and to the side of pointed tip 115.

FIG. 7H is an end-perspective-view drawing of the left-hand end of steel tube 757 after being partially flattened with a taper, then ground or sanded to a point, and two transverse drill holes 110 drilled through the top and bottom walls, and through the left- and right-hand walls (forming four side-wall holes 110 in addition to the two end holes 119).

FIG. 7I1 is a side-perspective-view drawing of the injection end of completed steel-tube carpet-odor-treatment device 706 after being partially flattened with a taper, and then ground or sanded to a point, which results in two angled openings 119 that emit fluid at about a 30-degree angle to one another forward and to the side of pointed tip 115 and four side-wall holes 110 (pointing up, down, left and right) with wooden ball 753 positioned to apply force in a left-to-right-hand direction to insert tip through the carpet.

FIG. 7I2 is a side-perspective-view drawing of the injection end of completed steel tube carpet-odor-treatment device 706 with wooden ball 753 positioned to apply lifting force in an upward direction to raise the carpet so fluid can be dispensed below the carpet.

FIG. 7I3 is an enlarged side-perspective-view drawing of the injection end of completed steel tube carpet-odor-treatment device 706 showing one of two angled openings 119 and two of the four side-wall holes 110 (pointing up and left).

FIG. 7J is a photograph of the injection end of completed steel-tube carpet-odor-treatment device 706 showing the six streams of fluid—two squirting out at about a 30-degree angle to one another forward from the tip and four side streams (pointing up, down, left and right).

FIG. 8A is a drawing of a first operation 800A of a method 800 according to some embodiments of the invention.

FIG. 8B is a drawing of a second operation 800B of method 800 according to some embodiments of the invention.

FIG. 8C is a drawing of a third operation 800C of method 800 according to some embodiments of the invention.

FIG. 8D is a drawing of a fourth operation 800D of method 800 according to some embodiments of the invention.

FIG. 8E is a drawing of a fifth operation 800E of method 800 according to some embodiments of the invention.

DETAILED DESCRIPTION OF THE INVENTION

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Figure 1A:
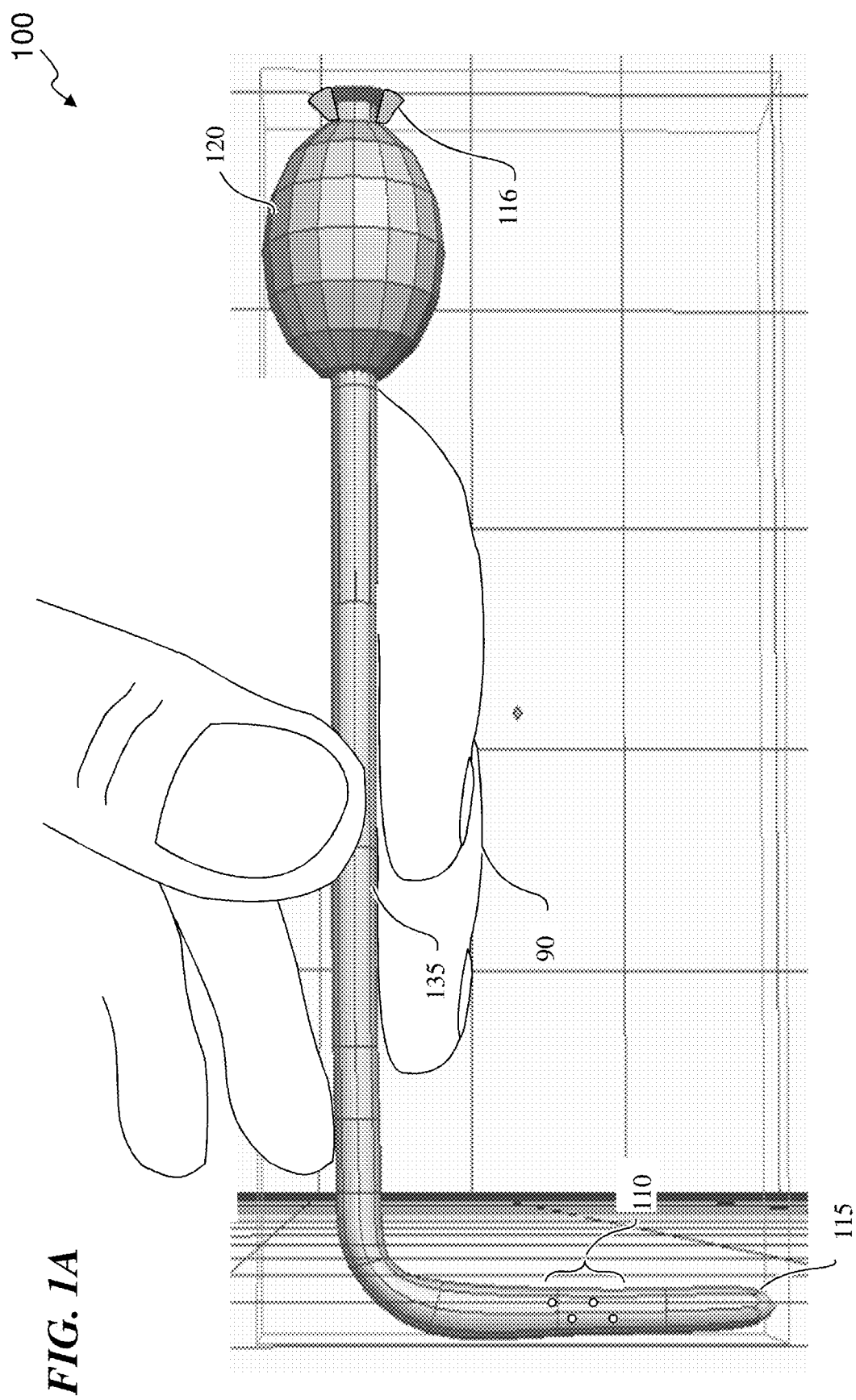
FIG. 1A is a side-view drawing of a carpet-odor-treatment device 100.

FIG. 1A is a side-view drawing of a carpet-odor-treatment device 100, according to some embodiments of the invention. The thumb and fingers of a user 90 are shown holding device 100. In some embodiments, device 100 is used to treat an odor of a carpet (e.g., by squirting anti-odor liquid, from below the carpet, into/onto the carpet, backing, pad, and/or floor). In some embodiments, device 100 is configured to provide an injection apparatus for injecting an odor-neutralizing and/or stain-removing fluid into a carpet (e.g., in some embodiments, device 100 is configured to inject the fluid into the space between the bottom surface of the carpet and the padding layer located directly below the carpet). In some embodiments, device 100 is configured to inject an odor-neutralizing fluid into a flooring material other than carpet. In some embodiments, device 100 is configured to inject an odor-neutralizing fluid into a suitable non-flooring material such as upholstery or the like. In some embodiments, device 100 is configured to inject an odor-neutralizing and/or stain-removing fluid such as urineOFF® (www.urineoff.com), Nature's Miracle Pet Stain & Odor Remover (www.natures-miracle.com/products/pet-odor-stain-removers/original-pet-stain-odor-remover.aspx), or the like. In some embodiments, device 100 is configured to inject fluid other than odor-neutralizing and/or stain-removing fluid (e.g., a stiffening polymer such as Golden-GAC 400 Acrylic Polymer (http://store.academyart.edu/paints-mediums/acrylic-painting-mediums/gac-400-acrylic-polymer-for-stiffening-fabrics.html)). In some embodiments, device 100 includes a hollow tube 135 that is approximately "L"-shaped. In other embodiments, tube 135 is any other suitable shape such that device 100 can be easily inserted into carpet. In some embodiments, device 100 includes a pointed penetration tip 115 at a first end of device 100 and a lip 106 at an opposite second end of device 100 distal from tip 115.

In some embodiments, device 100 includes a plurality of injection holes 110 located near the first end of device 100 and configured to provide exit ports for fluid that is inserted into device 100 at the second end of device 100. In some embodiments, injection holes 110 are positioned in a plurality of radial directions around tube 135 such that fluid inserted into device 100 exits device 100 in a plurality of radial directions. In some embodiments, injection holes 110 are positioned in any other suitable manner on tube 135. In some embodiments, device 100 is configured to provide a coverage area for the injected fluid of about 6 square inches, about 6.5 square inches, about 7 square inches, about 7.5 square inches, about 8 square inches, about 8.5 square inches, about 9 square inches, or, in some embodiments a coverage area that ranges between any two of the values listed above.

In some embodiments such as shown in FIG. 1A, device 100 includes a spherical lug 120 (in some embodiments, lug 120 has a suitable shape to provide its two functions—namely pushing tip 115 through carpet 99, and lifting the carpet to provide plenty of space beneath the carpet or between the carpet and its pad underneath it; in some other embodiments, a cylindrical shape (e.g., lug 121 of FIG. 1B or 120 of FIG. 1C) provides a relatively flat surface (the flat end of the cylindrical lug 120 of FIG. 1C, which is hammered on) that can be positioned perpendicular to shaft 135, and parallel to the axis of the bottom end 111 of tube 135 to apply force along the longitudinal axis of end 111 (see FIG. 1C), and a rounded grasping surface to hold while lifting the carpet; in other embodiments, any other suitable shape can be used). In some embodiments, lug 120 is cylindrically shaped and has a hollow inner portion configured to fit around tube 135 such that lug 120 can be slid up and down tube 135. In some embodiments, lug 120 has any other suitable shape. In some embodiments, lug 120 is configured to provide a handle or grip for device 100 such that device 100 can be lifted up during the injection of an odor-neutralizing fluid into carpet (in some embodiments, the lifting of device 100 during fluid injection pulls the carpet up and away from the carpet padding near the area of insertion of device 100 such that a "dome" of carpet is pulled away from the carpet padding to allow increased coverage area for the injected fluid). In some embodiments, in order to lift device 100 using lug 120, lug 120 is pulled to the second end of device 100 until it reaches lip 106, which prevents it from being pulled completely off of device 100. In some embodiments, lug 120 is further configured to provide a surface area that can be used to hammer or otherwise force device 100 into the carpet. In some embodiments, lug 120 is fixedly attached to device 100 and lip 106 is removed (e.g., in some embodiments, lug 120 is welded to tube 135).

In some embodiments, tube 135 is made from a single piece of material and is bent into the approximate "L" shape. In other embodiments, tube 135 is made from two or more pieces that are welded together (e.g., in some such embodiments, tube 135 includes a first piece that contains lip 106, a second piece that is welded to the first piece such that the first and second piece share the same longitudinal axis, and a third piece that includes injection holes 110 and tip 115 and is welded to the second piece such that the longitudinal axis of the third piece is perpendicular to the longitudinal axis of the first and second pieces (in some such embodiments tip 115 is itself welded to the end of the third piece)).

Figure 1B:
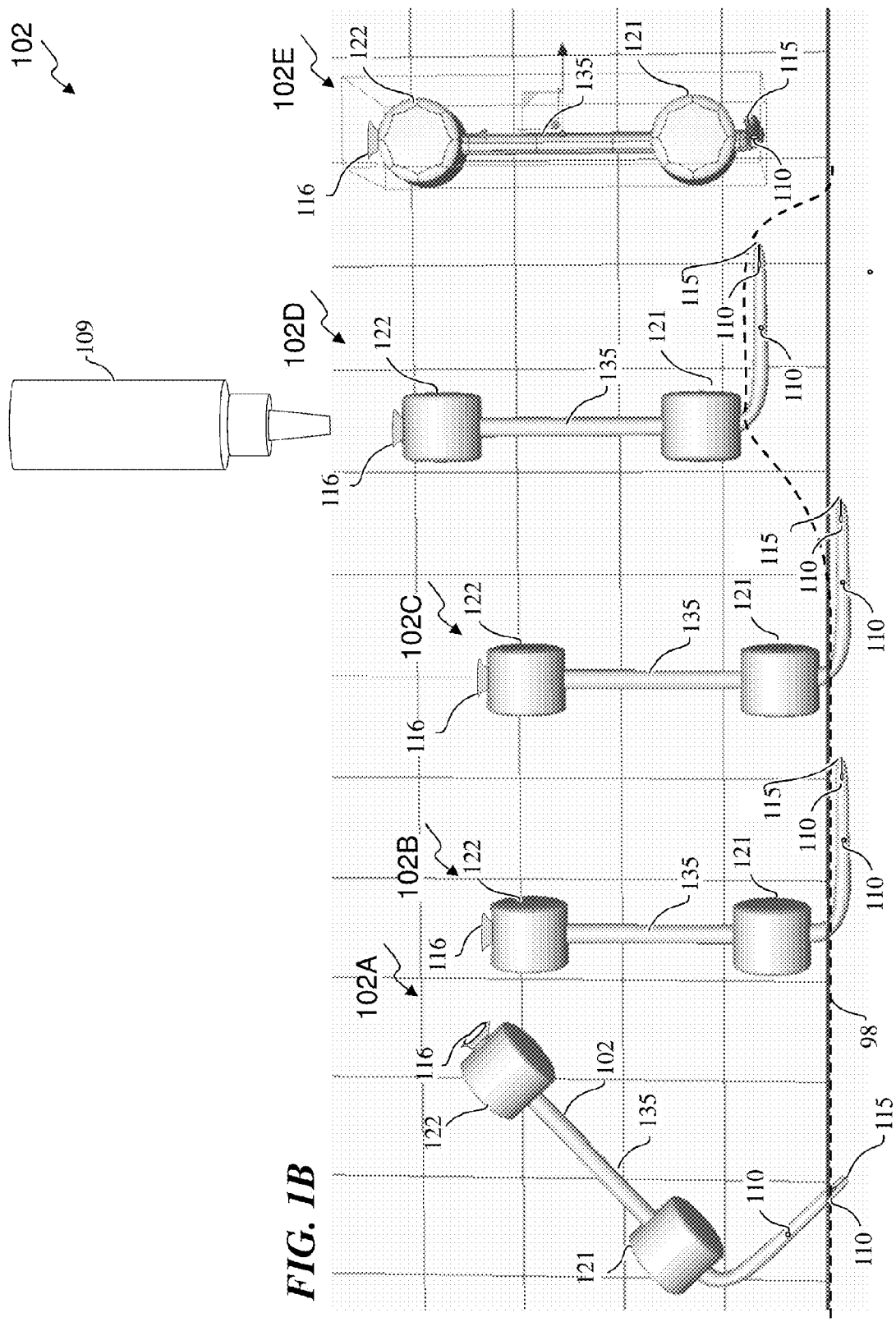
FIG. 1B is a side-view drawing of a carpet-odor-treatment device 102 in six different positions for carpet treatments relative to a carpet 99 shown in cross section.

FIG. 1B is a side-view drawing of a carpet-odor-treatment device 102 in six different positions for carpet treatments relative to a carpet 99 shown in cross section. At position 102A, device 102 is pushed or hammered downward at a non-perpendicular angle to carpet 99 to force a small hole through the backing 98 via pointed tip 115. In this embodiment, two lugs 120 (separately referred to as lug 121 and lug 122) are provided, and lug 121 is affixed to the bottom end of tube 135 and used as a hammer target to receive blows from a hammer or similar tool, or from the hand of the user 90, while lug 122 is affixed to the top end of tube 135 and used as a lifting element. At position 102B (which is identical to position 102C), device 102 has been inserted so end 111 is below carpet 99. At position 102D, the user 90 of device 102 has lifted carpet 99 inserted fluid from bottle 109 can be forced into funnel shaped opening 106, through tube 135 and out from holes 110 thus dispensing the fluid to the bottom of carpet 99 and to the top surface of any pad beneath carpet 99. At position 102E, the user 90 of device 102 has rotated device 102 to a position about 90 degrees from position 102D to dispense fluid at that area. The user can then continue to rotate device 102 to successive positions around the initial hole through which point 115 was forced, thus applying the deodorizing fluid to a large under-carpet area. Device 102 is then removed and the carpet will lie down to its original position. If an even larger area is to be treated, the device 102 can be inserted through the carpet in nearby positions.

Figure 1C:
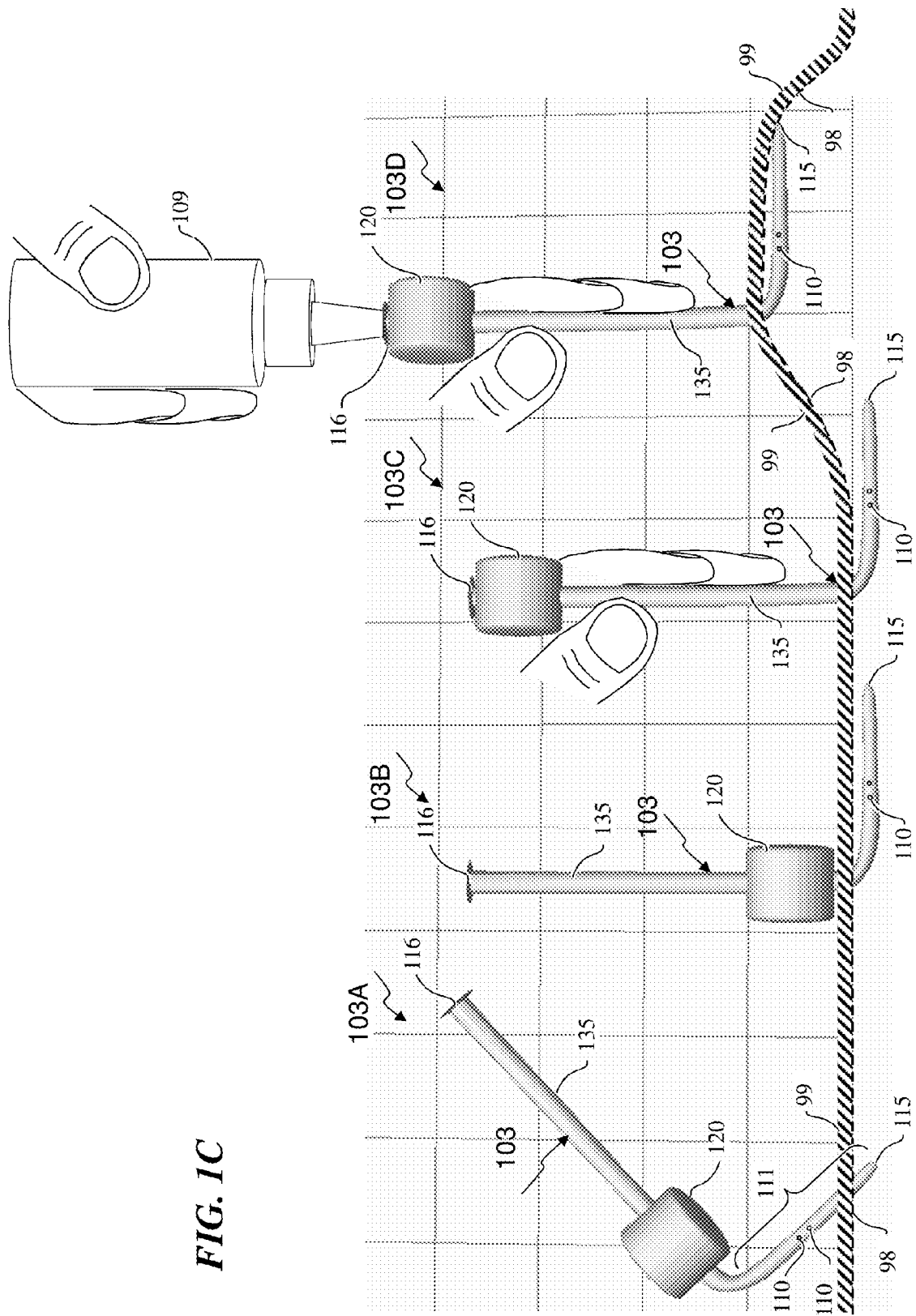
FIG. 1C is a side-view drawing of a carpet-odor-treatment device 103 in four different positions for carpet treatments relative to a carpet 99 shown in cross section.

FIG. 1C is a side-view drawing of a carpet-odor treatment device 103 in four different positions for carpet treatments relative to a carpet 99 shown in cross section. At position 103A, device 103 is pushed or hammered downward at a non-perpendicular angle to carpet 99 to force a small hole through the backing 98 via pointed tip 115. In this embodiment, a single slidable lug 120 is provided, and lug 120 is slid to the bottom end of tube 135 and used as a hammer target to receive blows from a hammer or similar tool, or from the hand of the user 90. Then, lug 120 is slid to the top end of tube 135 and used as a lifting element. At position 103B device 103 has been inserted so end 111 is below carpet 99. At position 103C, the user 90 of device 103 has slid lug 120 to the top end of tube 135. At position 103D, the user 90 of device 103 has lifted carpet 99, and inserted fluid from bottle 109 can be forced into funnel-shaped opening 116, through tube 135 and out from holes 110 thus dispensing the fluid to the bottom of carpet 99 and to the top surface of any pad beneath carpet 99. The user 90 of device 103 can then rotate device 103 to other positions (e.g., successively about 90 degrees from position 102D) to dispense fluid at those areas. Device 103 is then removed and the carpet will lie down to its original position. If an even larger area is to be treated, the device 103 can be inserted through the carpet in nearby positions.

Figure 1D:
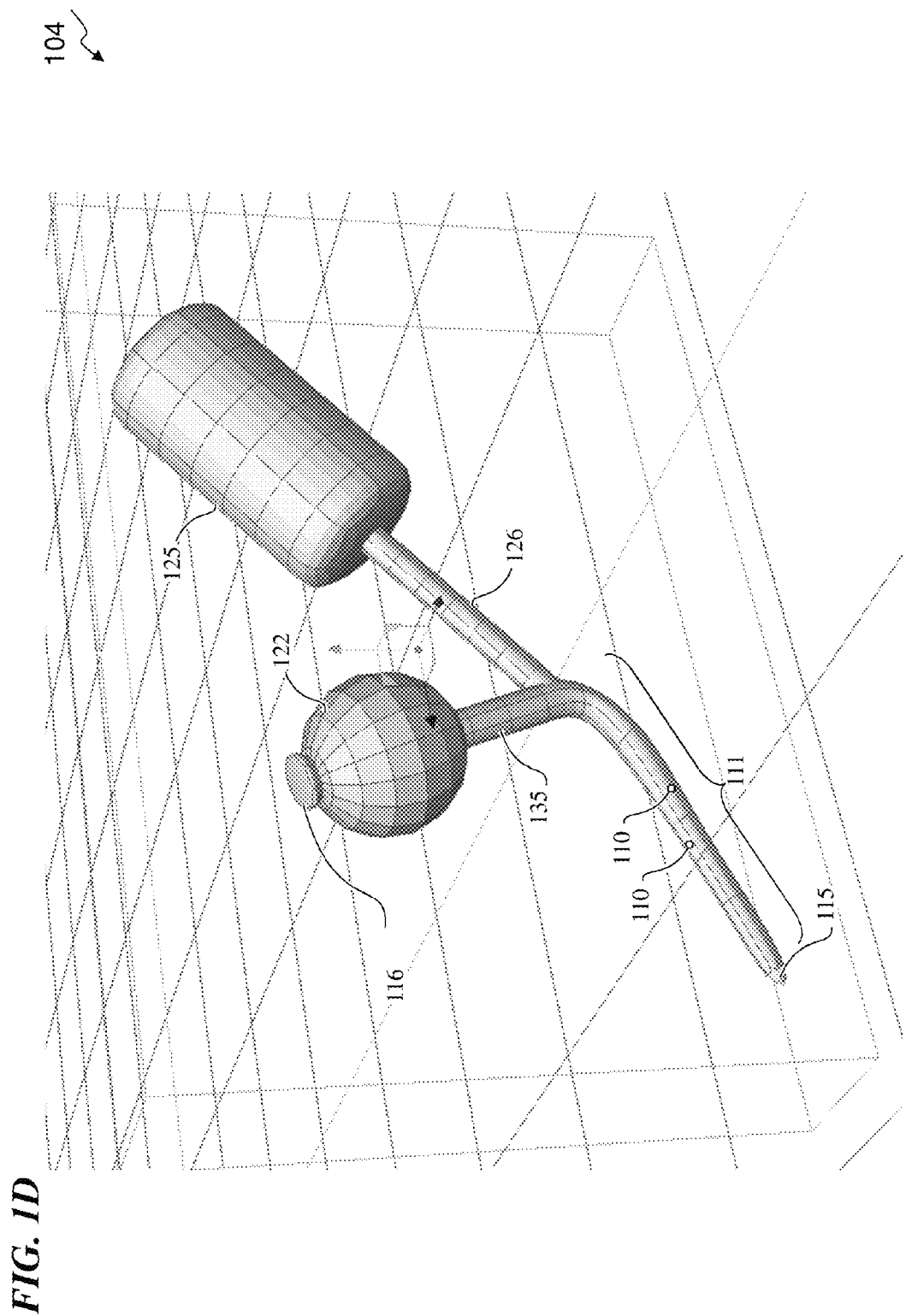
FIG. 1D is a perspective-view drawing of a carpet-odor-treatment device 104 for carpet treatments of a carpet 99.

FIG. 1D is a perspective-view drawing of a carpet-odor-treatment device 104 for carpet treatments of a carpet 99. In some embodiments, device 104 includes a handle 125 attached to a short shaft 126, which in turn is attached near the bottom of tube 135, in order to provide an easy-to-use handle to force tip 115 through the carpet 99. Other aspects of this figure are the same as described above for FIG. 1B.

Figure 1E:
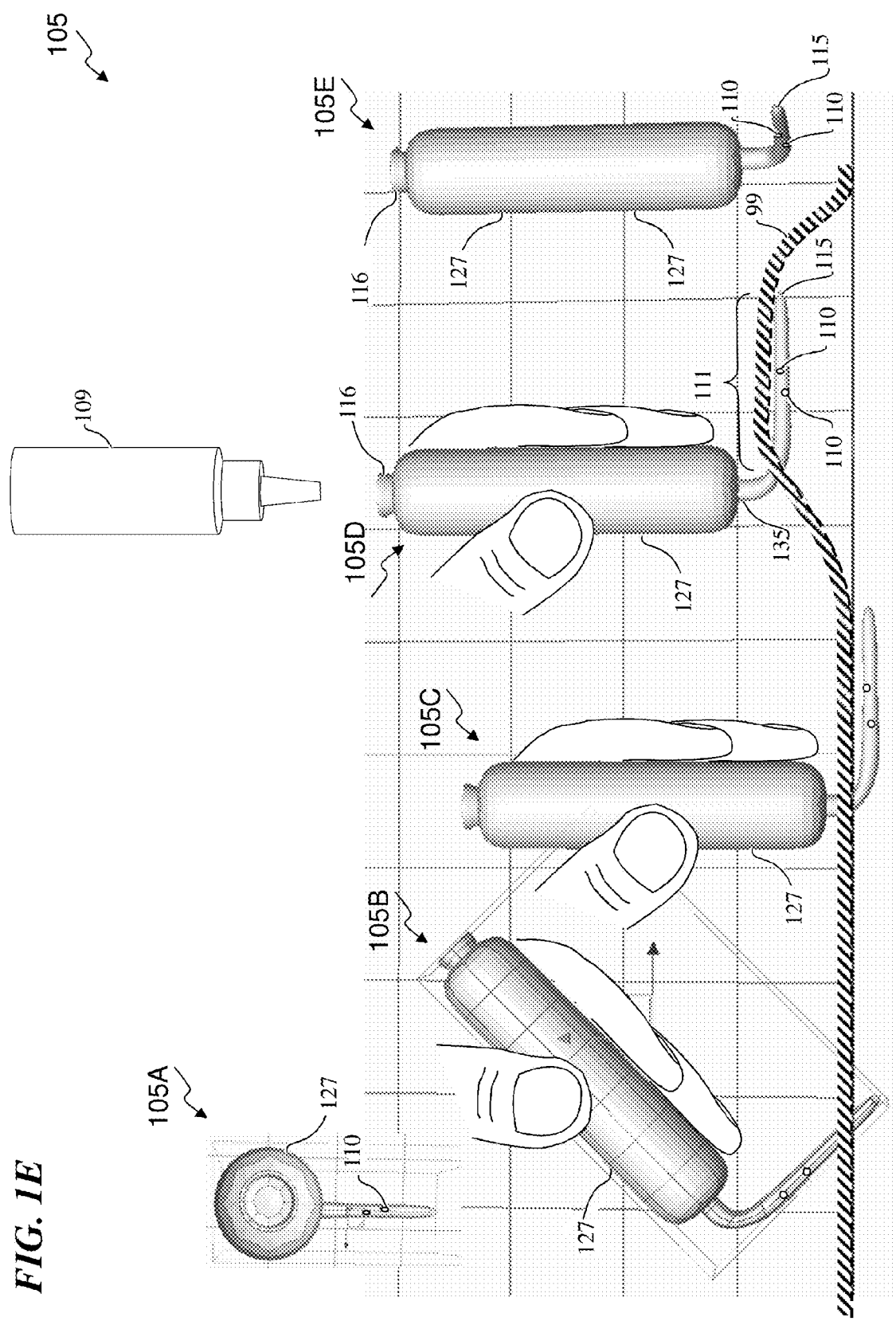
FIG. 1E is a side-view drawing of a carpet-odor-treatment device 105 in five different positions for carpet treatments relative to a carpet 99 shown in cross section.

FIG. 1E is a side-view drawing of a carpet-odor-treatment device 105 in five different positions for carpet treatments relative to a carpet 99 shown in cross section. In some embodiments, a single handle 127 provides both the insertion (providing a hand grip for forcing the tip 115 through the carpet) and the lifting functions (providing a hand grip for lifting lower end 111 and 115 to lift the carpet), and the longitudinal axis of handle 127 will be approximately perpendicular to the plane of the floor when lifting the carpet. Position 105A is a top view of device 105, while positions 105B, 105C, 105D, and 105E correspond to positions 102A, 102B, 102D, and 102E, respectively, described above for FIG. 1B.

Figure 1F:
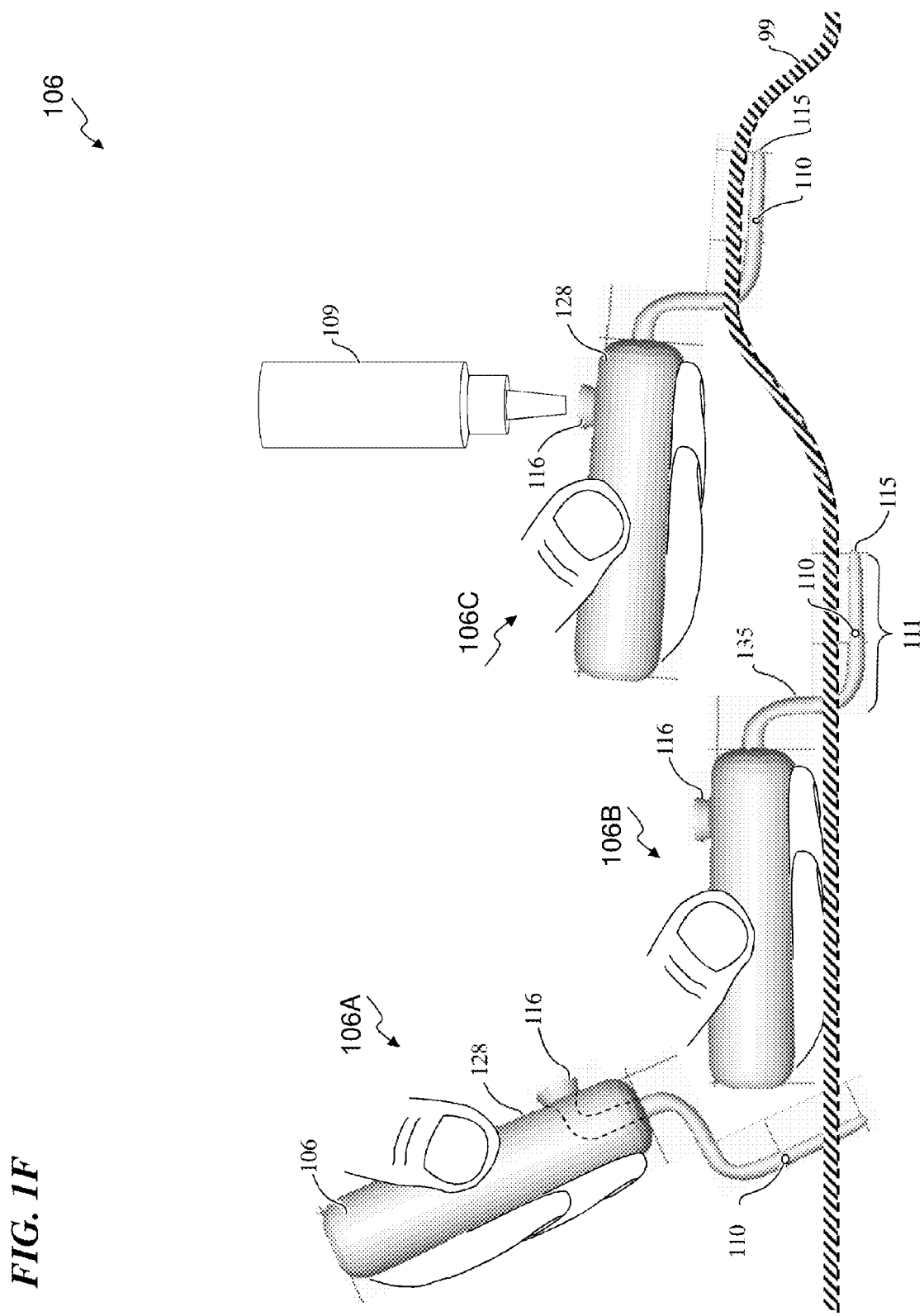
FIG. 1F is a side-view drawing of a carpet-odor-treatment device 106 in three different positions for carpet treatments relative to a carpet 99 shown in cross section.

FIG. 1F is a side-view drawing of a carpet-odor-treatment device 106 in three different positions for carpet treatments relative to a carpet 99 shown in cross section. Device 106 is similar to device 105 and is operated in a similar manner, except that handle 128 is arranged at a 90-degree angle (as compared to handle 127), and its longitudinal axis will be approximately parallel to the plane of the floor when lifting the carpet.

FIG. 2A1 is a side-view diagram of a carpet-odor-treatment system 201 that includes carpet-odor treatment device 211 and deodorizer-fluid-dispensing squeeze bottle 109. In some embodiments, device 211 has two lugs—one affixed at the bottom for inserting the pointed tip through the carpet and another affixed at the top for lifting the carpet, substantially as described above for FIG. 1B.

FIG. 2A2 is a top-view diagram of carpet-odor-treatment device 211.

FIG. 2A3 is a front-view diagram of carpet-odor-treatment device 211.

FIG. 2B1 is a side-view schematic diagram of a carpet-odor-treatment device 212. In some embodiments, device 212 has a single slidable lug that can be moved and used at one of two positions—one at the bottom for inserting the pointed tip through the carpet and another affixed at the top for lifting the carpet, substantially as described above for FIG. 1C. Note that flared end 233 serves as a stop to keep lug 222 from coming off when lifting the carpet, as well as a funnel for receiving fluid from squeeze bottle 109 (see FIG. 2A1).

In some embodiments, device 212 is substantially similar to device 100 described for FIG. 1A. In some embodiments, tube 135 and lug 222 are made from a material that includes stainless steel. In some embodiments, tube 135 and lug 222 are made from any other suitable material (e.g., a polymer material such as polyvinyl chloride (PVC)). In some embodiments, penetration tip 115 is made from a material that includes brass. In some embodiments, tip 115 is made from any other suitable material. In some embodiments, tip 115 is made by taper-flattening the end of steel tube 135 and grinding it to a point. In some embodiments, device 212 has the dimensions shown in FIG. 2B1. (In FIG. 2B1, "R" designates radius.) In other embodiments, device 212 has any other suitable dimensions. In some embodiments, substantially the dimensions and materials shown in FIG. 2B1 are used for each of the devices described herein.

In some embodiments, device 212 is referred to as "the Injectinator™". In some embodiments, device 212 increases the effectiveness of odor-neutralizer application by 80%. In some embodiments, device 212 is configured to last over hundreds of applications (in some embodiments, over thousands of applications). In some embodiments, device 212 is configured to inject odor-neutralizing fluid from a 4-ounce applicator bottle. In some embodiments, device 212 is configured to inject odor-neutralizing fluid from any other suitable-sized applicator bottle. In some embodiments, device 212 is configured to target pet odor at the source of the odor.

FIG. 2B2 is a top-view diagram of carpet-odor-treatment device 212.

FIG. 2B3 is a front-view diagram of carpet-odor-treatment device 212.

FIG. 2C1 is a side-view diagram of a carpet-odor-treatment system 206 that includes carpet-odor-treatment device 216 and deodorizer-fluid-dispensing squeeze bottle 109. Device 216 is similar to device 212 in FIG. 2B2 and device 103 of FIG. 1C, except that lug 242 has three functions—namely the tip-forcing function and lifting function of lug 120 of FIG. 1C and lug 222 of FIG. 2B2, plus the additional function of serving as a funnel (via tapered (e.g., in some embodiments, cone-shaped) end opening 243) that directs fluid into small flared end 236 (which is smaller than, and thus less expensive to form than, flared end 223 of FIG. 2A1), wherein small flared end 236 is large enough to serve as a stop to keep lug 233 from separating from the device. Thus, the flared end of tube 235 and the funnel-shaped end of lug 242 act together to receive fluid and provide a substantially sealed connection so fluid does not leak at the top of device 216.

FIG. 2C2 is a top-view diagram of carpet-odor-treatment device 216.

FIG. 2C3 is a front-view diagram of carpet-odor-treatment device 216.

FIG. 2C4 is a side-view diagram of a carpet-odor-treatment device combination funnel-shaped-fluid-receiving, force-delivery and lifting element 242.

FIG. 3 is a perspective side-view diagram of a cylindrical carpet-odor-treatment device combination force-delivery and lifting element 232, wherein its through-hole 238, through which the tube 135 is arranged, is along the cylinder axis of element 232. The length of cylinder 232 can be short as shown here, and slid to one of two positions for use (as described for FIG. 1C), or made much longer to be used in a single position for both the tip-forcing function and the lifting function, as described for FIG. 1E.

FIG. 4 is a side-view diagram of a cylindrical carpet-odor-treatment device combination force-delivery and lifting element 233—its description continues below.

FIG. 5 is a top-view diagram of a cylindrical carpet-odor-treatment device combination force-delivery and lifting element 233. In some embodiments, combination force-delivery and lifting element 233 includes a flat face for receiving impacts for the tip-forcing function, and two finger-fitting side wings configured to allow the user to have a larger finger-gripping area than is available with device 120 of FIG. 1C.

FIG. 6 is a block diagram of a method for using device 103 to treat a carpet with an odor-neutralizing fluid. In some embodiments, at block 605, pointed penetration tip 115 is used to insert device 103 into the carpet (in some embodiments, device 103 is hammered into the carpet by placing lug 120 near the bend in tube 135 and striking lug 120). In some embodiments, at block 610, lug 120 is moved to lip 116 of device 103 and device 103 is lifted such that a "dome" of carpet is lifted off of the carpet padding located underneath the carpet (in some embodiments, the carpet "dome" increases the coverage area of the fluid injected via device 103). In some embodiments, at block 615, odor-neutralizing fluid is inserted into device 103 at the end of device 103 near lip 116 by placing the tip of an applicator bottle 109 into the hollow portion of tube 135 and squeezing the applicator bottle such that fluid in the applicator bottle is passed through tube 135 and injected (via holes 110) into the area underneath the carpet "dome". In some embodiments, at block 620, device 103 is removed from the carpet.

FIG. 7A is a side-view photograph of an open-ended steel tube 751 before further processing according to some embodiments of the present invention. In some embodiments, tube 751 has an outer diameter of about 3/16 inch. In some embodiments, tube 751 has an outer diameter of about 1/4 inch. In some embodiments, tube 751 has an outer diameter of between about 3/16 inch and about 1/4 inch. In other embodiments, devices and components having other suitable dimensions are used.

FIG. 7B is a side-view photograph of an open-ended steel tube 752 after a flare has been formed at the right-hand end.

FIG. 7C is an end-view photograph of a wooden ball 753 (e.g., used as lug 120 of FIG. 1C) having a through-hole that has been drilled through a polished spherical-shaped piece of wood approximately 25 mm (about 1 inch) in diameter.

FIG. 7D is an end-view photograph of open-ended steel tube 754 after a flare has been formed at the right-hand end, a wooden ball 753 having a through-hole fitted over the tube 754, and a rounded bend of about 90 degrees formed near the left-hand end. Ball 753 is thus trapped between the flared end and the 90-degree bend.

FIG. 7E is an end-perspective-view drawing of the left-hand end of steel tube 754.

FIG. 7F is an end-perspective-view drawing of the left-hand end of steel tube 755 after being partially flattened with a taper (e.g., hammered to flatten the center walls so they are flat against one another, leaving a small opening on either side that can be opened by the next grinding operation below).

FIG. 7G is an end-perspective-view drawing of the left-hand end of steel tube 756 after being partially flattened with a taper, and then ground or sanded to a point, which results in two angled openings 119 that emit fluid at about a 30-degree angle to one another forward and to the side of pointed tip 115. These openings shoot fluid in an outward radial direction from the hole formed in the carpet.

FIG. 7H is an end-perspective-view drawing of the left-hand end of steel tube 757 after being partially flattened with a taper, then ground or sanded to a point, and two transverse drill holes 110 drilled through the top and bottom walls, and through the left- and right-hand walls (forming four side-wall holes 110 in addition to the two end holes 119). These six holes provide a wide spray area. In some embodiments, additional holes can be drilled or punched into the tubing, or other spray formations are formed.

FIG. 7I1 is a side-perspective-view drawing of the injection end of completed steel-tube carpet-odor-treatment device 706 after being partially flattened with a taper, and then ground or sanded to a point, which results in two angled openings 119 that emit fluid at about a 30-degree angle to one another forward and to the side of pointed tip 115 and four side-wall holes 110 (pointing up, down, left and right) with wooden ball 753 positioned to apply force in a left-to-right-hand direction to insert the tip through the carpet.

FIG. 7I2 is a side-perspective-view drawing of the injection end of completed steel-tube carpet-odor-treatment device 706 with wooden ball 753 positioned to apply lifting force in an upward direction to raise the carpet so fluid can be dispensed below the carpet.

FIG. 7I3 is an enlarged side-perspective-view drawing of the injection end of completed steel-tube carpet-odor-treatment device 706 showing one of two angled openings 119 and two of the four side-wall holes 110 (pointing up and left).

FIG. 7J is a photograph of the injection end of completed steel-tube carpet-odor-treatment device 706 showing the six streams of fluid—two squirting out at about a 30-degree angle to one another forward from the tip and four side streams (pointing up, down, left and right).

FIG. 8A is a drawing of a first operation (or step 1) 800A of a method 800 according to some embodiments of the invention. In this first operation (or step 1), one hand holds the shaft of the Injectinator™ vertical with the flare end facing up (will be in this position the entire time), allowing the lug to fall down the shaft (lug will be used to tap the Injectinator™ into the carpet and through the backing with the other hand). The dimensions shown represent only one embodiment; other embodiments use other suitable dimensions.

FIG. 8B is a drawing of a second operation (or step 2) 800B of method 800 according to some embodiments of the invention. In this second operation (or step 2), tapping on the lug adjusts the tip of the Injectinator™ through the carpet and carpet backing.

FIG. 8C is a drawing of a third operation (or step 3) 800C of method 800 according to some embodiments of the invention. In this third operation (or step 3), the "lower arm" of the approximately "L"-shaped Injectinator™ (including the Injectinator™ tip) is under the carpet, between the carpet backing and carpet pad.

FIG. 8D is a drawing of a fourth operation (or step 4) 800D of method 800 according to some embodiments of the invention. In this fourth operation (or step 4), the sliding lug is lifted up, thus "doming out" the carpet, making room between the carpet backing and carpet pad so odor neutralizer can be easily distributed to the affected area.

FIG. 8E is a drawing of a fifth operation (or step 5) 800E of method 800 according to some embodiments of the invention. In this fifth operation (or step 5), the lug of the Injectinator™ is lifted with one hand (this will "dome" the carpet), and the other hand squeezes odor neutralizer from applicator bottle 809 of odor-neutralizing fluid into the flared end of tool, distributing fluid through the tool to the affected area between the backing of the carpet and the carpet pad. The Injectinator™ tool is then pulled out of the carpet, and the carpet surface may be blotted.

In some embodiments, the present invention provides a carpet-treatment apparatus that includes a hollow tube having a first end and a second end; a fluid-receiving orifice located at the first end of the tube; a plurality of injection holes located near the second end of the tube; a pointed tip located at the second end of the tube, and configured for insertion through the carpet from an upper face of the carpet until the plurality of injection holes are located under a lower face of the carpet; and a lug having an opening therethrough, wherein the tube passes through the opening in the lug and is configured to increase the surface area of the tube.

Some embodiments of the apparatus further include a squeeze bottle having a fluid-ejection nozzle shaped to be at least partially inserted into the fluid-receiving orifice located at the first end of the tube, in order to force fluid into and through the tube and out the plurality of injection holes located under the carpet.

In some embodiments of the apparatus, a first length of the tube at the first end is substantially perpendicular to a second length of the tube at the second end, and wherein the lug slides along the first length and is shaped to be grabbed by a user and pulled vertically upward from the first end of the tube to lift the carpet after the second end is inserted through the carpet and the second length is substantially horizontal under the carpet.

In some embodiments of the apparatus, the lug is configured to be slidably movable along the first length of the tube such that the lug is positioned closer to the second end for the insertion through the carpet from an upper face of the carpet until the plurality of injection holes are located under a lower face of the carpet, and then moved closer to the first end of the tube to lift the carpet after the second end is inserted through the carpet and the second length is substantially horizontal under the carpet.

In some embodiments of the apparatus, the lug has a surface configured to be hammered on by another object to force the pointed tip through the carpet.

In some embodiments of the apparatus, lug has a cylindrically shaped end with a substantially flattened face for receiving hammer blows.

Some embodiments of the apparatus further include a squeeze bottle having a fluid-ejection nozzle shaped to be at least partially inserted into the fluid-receiving orifice located at the first end of the tube.

In some embodiments, the present invention provides a method for treating carpet that includes providing a hollow tube having a first end and a second end, wherein the tube includes: a plurality of injection holes located near the second end of the tube, a fluid-receiving orifice located at the first end of the tube, a pointed tip located at the second end of the tube, and a lug moveably attached to the tube; inserting the tube into a carpet by penetrating the pointed tip through the carpet; lifting the tube up via the lug such that a portion of the carpet is pulled away from padding located underneath the carpet; receiving fluid into the tube at the first end of the tube; and injecting the fluid under the carpet via the injection holes.

In some embodiments of the method, a first length of the tube at the first end is substantially perpendicular to a second length of the tube at the second end, the method further including: sliding the lug along the first length away from the first end before penetrating the pointed tip through the carpet; and grabbing the lug by a user and pulling vertically upward from the first end of the tube to lift the carpet after penetrating the pointed tip through the carpet and after locating the second length substantially horizontal under the carpet.

In some embodiments of the method, the lug is configured to be slidably movable along the first length of the tube such that the lug is positioned closer to the second end for the insertion through the carpet from an upper face of the carpet until the plurality of injection holes are located under a lower face of the carpet, and then moved closer to the first end of the tube to lift the carpet after the second end is inserted through the carpet and the second length is substantially horizontal under the carpet.

Some embodiments of the method further include hammering on a surface of the lug by another object to force the pointed tip through the carpet.

In some embodiments of the method, lug has a cylindrically shaped end with a substantially flattened face for receiving hammer blows.

Some embodiments of the method further include forcing fluid from a squeeze bottle having a fluid-ejection nozzle into the fluid-receiving orifice located at the first end of the tube.

Some embodiments of the method further include forcing fluid from a squeeze bottle having a fluid-ejection nozzle into the fluid-receiving orifice located at the first end of the tube, in order to force fluid into and through the tube and out the plurality of injection holes located under the carpet.

In some embodiments, the present invention provides a carpet-treatment device that includes tube means for transporting fluid into a carpet, wherein the tube means includes: means for inserting the tube means through the carpet; and means for lifting the tube means up such that a portion of the carpet is pulled away from padding located underneath the carpet.

In some embodiments of the device, a first length of the tube means at a first end is substantially perpendicular to a second length of the tube means at a second end, and wherein the means for lifting includes a lug that slides along the first length and is shaped to be grabbed by a user and pulled vertically upward from the first end of the tube to lift the carpet after the second end is inserted through the carpet and the second length is substantially horizontal under the carpet.

In some embodiments of the device, the lug is configured to be slidably movable along the first length of the tube such that the lug is positioned closer to the second end for the insertion through the carpet from an upper face of the carpet until the plurality of injection holes are located under a lower face of the carpet, and then moved closer to the first end of the tube to lift the carpet after the second end is inserted through the carpet and the second length is substantially horizontal under the carpet.

In some embodiments of the device, the lug has a surface configured to be hammered on by another object to force the pointed tip through the carpet.

In some embodiments of the device, lug has a cylindrically shaped end with a substantially flattened face for receiving hammer blows.

Some embodiments of the device further include means for forcing fluid a fluid-receiving orifice located at the first end of the tube means, in order to force fluid into and through the tube means and out a plurality of injection holes in the tube means located under the carpet.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment). Further, some embodiments include fewer than all the components described as part of any one of the embodiments described herein.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," etc., are used merely as labels, and are not intended to impose numerical requirements on their objects.

What is claimed is:

1. A method for treating a carpet comprising:
   providing a hollow tube having a first end and a second end, wherein the hollow tube includes:
      a plurality of injection holes located near the second end of the hollow tube,
      a fluid-receiving orifice located at the first end of the hollow tube;
      a pointed tip located at the second end of the hollow tube, and
      a lug moveably attached to the hollow tube;
   inserting the hollow tube into the carpet by penetrating the pointed tip through the carpet;
   lifting the hollow tube up via the lug such that a portion of the carpet is pulled away from padding located underneath the carpet;
   receiving a fluid into the hollow tube at the first end of the hollow tube; and
   injecting the fluid under the carpet via the plurality of injection holes.

2. The method of claim 1, wherein a first length of the hollow tube at the first end is substantially perpendicular to a second length of the hollow tube at the second end, the method further including:
   sliding the lug along the first length away from the first end before penetrating the pointed tip through the carpet; and
   grabbing the lug by a user and pulling vertically upward from the first end of the hollow tube to lift the carpet after penetrating the pointed tip through the carpet and after locating the second length substantially horizontal under the carpet.

3. The method of claim 2, wherein the lug is configured to be slidably movable along the first length of the hollow tube such that the lug is positioned closer to the second end for the insertion through the carpet from an upper face of the carpet until the plurality of injection holes are located under a lower face of the carpet, and then moved closer to the first end of the hollow tube to lift the carpet after the second end is inserted through the carpet and the second length is substantially horizontal under the carpet.

4. The method of claim 3, further comprising:
   hammering on a surface of the lug by another object to force the pointed tip through the carpet.

5. The method of claim 4, wherein the lug has a cylindrically shaped end with a substantially flattened face for receiving hammer blows.

6. The method of claim 5, further comprising:
   forcing fluid from a squeeze bottle having a fluid-ejection nozzle into the fluid-receiving orifice located at the first end of the hollow tube.

7. The method of claim 1, further comprising:
   forcing fluid from a squeeze bottle having a fluid-ejection nozzle into the fluid-receiving orifice located at the first end of the hollow tube, in order to force fluid into and through the hollow tube and out the plurality of injection holes located under the carpet.

* * * * *